(12) United States Patent
Gabbard et al.

(10) Patent No.: US 6,190,363 B1
(45) Date of Patent: Feb. 20, 2001

(54) SELF-ALIGNING PLUNGER ROD (75) Inventors: Mark E. Gabbard, Salisbury, MD (US); John J. Niedospial, Jr., Burlington, NJ (US); Timothy J. Gabbard, Salisbury, MD (US)

(73) Assignee: Bracco Diagnostics, Inc., Princeton, NJ (US)

( * ) Notice: Under 35 U.S.C. 154(b), the term of this patent shall be extended for 0 days.

(21) Appl. No.: 09/490,272

(22) Filed: Jan. 24, 2000

(51) Int. Cl.$^7$ .................................................. A61M 5/315
(52) U.S. Cl. ............................................................ 604/220
(58) Field of Search .................... 604/218–220, 604/221, 222, 228, 230, 235

(56) References Cited

U.S. PATENT DOCUMENTS

| | | | |
|---|---|---|---|
| 4,543,093 | 9/1985 | Christinger | 604/228 |
| 4,840,616 | * 6/1989 | Banks | 604/218 |
| 4,890,626 | * 1/1990 | Wang | 604/220 |
| 5,215,536 | * 6/1993 | Lampropoulos et al. | 604/187 |
| 5,222,942 | 6/1993 | Bader | 604/110 |
| 5,358,497 | * 10/1994 | Dorsey et al. | 604/220 |
| 5,485,853 | * 1/1996 | Stubbs | 604/220 |
| 5,700,247 | 12/1997 | Grimard et al. | 604/220 |
| 6,030,367 | * 2/2000 | Balestracci | 604/218 |

FOREIGN PATENT DOCUMENTS

| | | | |
|---|---|---|---|
| WO 91/00114 | 1/1991 | (WO) | 604/218 |
| WO 93/09827 | 5/1993 | (WO) | 604/229 |

* cited by examiner

*Primary Examiner*—Sharon Kennedy
(74) *Attorney, Agent, or Firm*—Imre Balogh

(57) ABSTRACT

A self-aligning plunger rod and a non-elastomeric plastic plunger insert assembly for use with an elastomeric plunger in a cartridge or syringe barrel for manual or power-assisted withdrawing of fluid from a site or expelling fluid from the cartridge or syringe barrel.

20 Claims, 12 Drawing Sheets

SELF-ALIGNING PLUNGER ROD

BACKGROUND OF THE INVENTION

1. Field of the Invention

This invention relates to a self-aligning plunger rod for use in a syringe or cartridge barrel having a plunger and containing a parenteral solution therein, or in a syringe or cartridge which are empty and are to be filled with a parenteral solution by the user at the time of administration.

The present invention also relates to a plunger rod for use in a syringe or cartridge containing a parenteral solution therein intended to be dispensed from a power injector.

2. Reported Developments

Syringes and cartridges made of glass or polymeric materials for dispensing parenteral solutions or withdrawing biological fluids from a patient are well known in the prior art. They comprise a cylindrical barrel with a tapered portion at one end to which a needle or luer connector can be attached, and an open end which is stoppered by a plunger of a resilient thermoplastic or elastomeric material. The plunger serves the function of a stopper, when the barrel is filled with a fluid, or as a slidable member to expel the fluid from the barrel or withdraw a biological fluid from a patient or another source.

In order to expel fluid from the barrel or withdraw fluid into the barrel, the plunger is moved toward the distal end or the proximal end of the barrel by a plunger rod which is attachable to the plunger typically by screw threads. The user exerts a force, manually or by the use of a power injector, on the plunger rod to push or pull the plunger in the barrel. While the plunger rod does not contact the fluid in the barrel, it serves a very important function: it causes the plunger to move in an axial direction back and forth in the barrel when an external force is applied thereon.

The force applied to the plunger by the plunger rod should be perpendicular to the plunger so that the force exerted on the wall of the barrel by the plunger is uniform around the 360° of its cylindrical configuration. When the plunger rod flexes in the barrel, the direction of force on the plunger will not be uniform resulting in pressure points at certain areas of contact between the plunger and the inside wall of the barrel and, conversely, inadequate pressure points at other parts of the interface between the plunger and the inside wall of the barrel. Such pressure differences tend to allow leakage and difficulty in moving the plunger at an even rate in the barrel.

Typical prior art devices have fixed connections between plunger rods and plungers; they are either one-piece combinations of plunger rods and plungers or two-piece combinations wherein the plunger rods are threaded into the plungers. Some plungers are equipped with rigid plastic inserts having internal threads therein in order to support the elastomeric plunger heads and to engage the plunger rods and hold them in an axial orientation. Both approaches allow some movement of the plunger rods in a lateral direction which may result in leakage of the medical fluid from the syringe barrel.

Recognizing the importance of dimensional stability, the prior art has incorporated various stability enhancing means into plunger rods which include the following.

The assembly disclosed in U.S. Pat. No. 4,543,093 has a plunger rod, the central portion of which is almost as large as the inside diameter of the syringe barrel so that it will assist in keeping the plunger rod assembly concentrically aligned within the syringe barrel.

WO 93/09827 discloses a shank having a plurality of longitudinal and radially extending vanes. In one preferred embodiment the shank is provided with four vanes in an "X" pattern, while in another preferred embodiment, the shank is provided with three vanes forming a "Y" pattern.

U.S. Pat. Nos. 5,700,247 and 5,860,961 disclose plunger rods having a plurality of vanes or support ribs.

A common feature of these plunger rods is a shank extending between the distal and proximal ends of the plunger rods having vanes or support ribs thereon. The vanes or support ribs are identical with one another running longitudinally on the shank and extending radially therefrom. This feature is an improvement over typical plunger rods in that the plunger rods have limited flexibility in the lateral direction, thereby exerting pressure on the plunger surface in an axial direction. However, we have found that even limited flexibility of the plunger rods allow lateral movement of the plungers in syringe barrels. This lateral movement of the plunger rods attached to plungers can cause leakage of fluid from the syringe barrels.

An object of the present invention is to provide a plunger rod and plastic plunger insert combination which directs the force exerted on the plunger rod in an axial direction. The elastomeric plunger placed on the plastic plunger insert will exert a uniform force on the inside wall of the syringe barrel thereby preventing leakage of the fluid content from the syringe barrel.

Another object of the present invention is to provide a reinforced plunger rod in combination with a plastic plunger insert which may be used either manually or in a power injector. Reinforced plunger rods without plastic plunger inserts are disclosed in co-pending application Ser. No. 09/273,901 filed on Mar. 22, 1999 which is incorporated herein by reference.

SUMMARY OF THE INVENTION

In accordance with the present invention there is provided a plunger rod and plastic plunger insert combination having a self-aligning feature wherein the plunger rod tip fits into the socket of the plunger insert and freely glides therein. This feature allows the plunger rod tip to float in the socket of the plastic plunger insert and eliminates lateral pressure on the plastic plunger insert. The plastic plunger insert is equipped with an elastomeric plunger which may be of various configurations.

The self-aligning plunge rod and plastic plunger insert combination comprises:

a) a plunger rod having a distal end and a proximal end comprising:
longitudinal radially extending vanes;
a thumb rest at the proximal end;
a disc at the distal end; and
a plunger rod tip extending from the disc at the distal end designed to engage a plastic plunger insert, said plunger rod tip comprising a neck portion and a ball portion, the ball portion having slots therein extending axially from the neck portion;

b) a non-elastomeric plastic plunger insert comprising:
a cylindrical shaft having a distal end and a proximal end;
a cone-shaped head extending from the distal end of the cylindrical shaft having an inside surface and an outside surface;
a cavity in the cone-shaped head defined by a cylindrical rim and the inside surface of the cone-shaped head;
a plurality of tabs extending from the cylindrical rim into the cavity; and a plurality of notches or openings between the tabs designed to receive the slotted ball portion of the plunger rod tip.

In use, the slots of the plunger rod tip are aligned with the notches or openings in the plastic insert. The ball portion of the plunger rod tip is inserted into the cavity of the plastic insert and rotated to engage the tabs of the plastic insert.

In a second embodiment of the present invention a reinforced plunger rod body is used in combination with the plunger rod tip and the plastic insert. The reinforced plunger rod body having a distal end and a proximal end comprises:

an end disc at the distal end;

a plunger rod tip extending from the end disc designed to engage a plastic plunger insert, said plunger rod tip comprising a neck portion and a ball portion, the ball portion having slots therein extending axially from the neck portion;

a thumb rest at the proximal end for facilitating exertion of external pressure on the plunger rod;

a reinforcing disc at about the longitudinal mid-point of the plunger rod;

a first pair of rectangular radially extending vanes connecting the end disc and the reinforcing disc;

a second pair of rectangular radially extending vanes connecting the reinforcing disc and the thumb rest;

a first pair of isosceles triangular radially extending vanes connecting the end disc and the reinforcing disc, wherein the smallest angle of the isosceles triangular vanes point toward the reinforcing disc; and a second pair of isosceles triangular radially extending vanes connecting the reinforcing disc and the thumb rest, wherein the smallest angle of the isosceles triangular vanes point toward the reinforcing disc, wherein:

said first pair of said rectangular radially extending vanes and said first pair of said isosceles triangular radially extending vanes are integral with each other and with said end disc and said reinforcing disc; and said second pair of said rectangular radially extending vanes and said second pair of said isosceles triangular radially extending vanes are integral with each other and with said reinforcing disc and said thumb rest.

In a third embodiment of the present invention, a reinforced plunger rod body of a different configuration from that of the reinforced plunger rod body of the second embodiment is used in combination with the plunger rod tip and the plastic insert.

The reinforced plunger rod having a distal end and a proximal end comprises:

an end disc at the distal end;

a plunger rod tip extending from the end disc designed to engage a plastic plunger insert, said plunger rod tip comprising a neck portion and a ball portion, the ball portion having slots therein extending axially from the neck portion;

a thumb rest at the proximal end for facilitating exertion of external pressure on the plunger rod;

a reinforcing disc at about the longitudinal mid-point of the plunger rod;

a first pair of rectangular radially extending vanes connecting the end disc and the reinforcing disc;

a second pair of rectangular radially extending vanes connecting the reinforcing disc and the thumb rest;

a first pair of isosceles triangular radially extending vanes connecting the end disc and the reinforcing disc, wherein the smallest angle of the isosceles triangular vanes point toward the reinforcing disc; and a second pair of isosceles triangular radially extending vanes connecting the reinforcing disc and the thumb rest, wherein the smallest angle of the isosceles triangular vanes point toward the reinforcing disc, wherein:

said first pair of said rectangular radially extending vanes and said first pair of said isosceles triangular radially extending vanes are integral with each other and with said end disc and said reinforcing disc; and said second pair of said rectangular radially extending vanes and said second pair of said isosceles triangular radially extending vanes are integral with each other and with said reinforcing disc and said thumb rest.

In use, the slots of the plunger rod tip are aligned with the notches or openings in the plastic insert. The ball portion of the plunger rod tip is inserted into the cavity of the plastic insert and rotated to engage the tabs of the plastic insert.

BRIEF DESCRIPTION OF THE DRAWINGS

FIG. 13A is a cross-sectional view of the reinforced plunger rod taken along the line 13A—13A of FIG. 13;

FIG. 13B is another cross-sectional view of the reinforced plunger rod taken along the line 13B—13B of FIG. 13;

FIG. 18A is a cross-sectional view of the reinforced plunger rod taken along the line 18A—18A of FIG. 18;

FIG. 18B is a cross-sectional view of the reinforced plunger rod taken along the line 18B—18B of FIG. 18;

DETAILED DESCRIPTION OF THE INVENTION

In the drawings, like numerals with ' or " denote the same parts of the device in different embodiments of the present invention.

Referring to FIGS. 1–4, a typical prior art plunger rod is shown in perspective, side elevational, bottom plan, and top plan views. Plunger rod 1 having a distal end 2 and a proximal end 3 comprises: longitudinal and radially extending vanes 4a, 4b, 4c and 4d (4d is hidden in the perspective view); a thumb rest 5 at the proximal end and a disc 6 at the distal end 2 of the plunger rod; and a screw threaded member 7 extending from disc 6 designed to engage a plunger. Vanes 4a, 4b, 4c and 4d are equivalent to one another extending from thumb rest 5 to disc 6. These vanes meeting at the center 8 of the plunger rod are of rectangular configuration.

The plunger rod is threaded into an elastomeric plunger which also contains thread means for engagement with the plunger rod. When the plunger rod joined with the plunger is inserted into the barrel of a syringe or cartridge to expel medical fluid contained in the barrel, the manual force exerted on the plunger rod will move the plunger towards the distal end of the barrel. However, this manual force has two components: a large force in the axial direction; and a smaller force in the lateral direction. This smaller force tends to cause non-uniform pressure points at certain areas of contact between the plunger and the inside wall of the barrel. Such pressure differences tend to allow leakage of the content of the barrel and creates difficulty in moving the plunger at an even rate in the barrel.

We have now discovered a plunger rod and plastic plunger insert combination having a self-aligning feature wherein the plunger rod tip fits into the socket of the plunger insert and freely glides therein. This feature allows the plunger rod tip to float in the socket of the plastic plunger insert and eliminates lateral pressure on the plastic plunger insert. This and other advantageous features will be explained in the description of the invention in reference to the drawings.

Referring to FIGS. 5–8, showing perspective, side elevational, bottom and top plan views, there is shown a plunger rod 8 (generally designated) having a distal end 10 and a proximal end 12 comprising: longitudinal radially extending vanes 14a, 14b, 14c and 14d (14d is hidden); a thumb rest 16 at the proximal end, and a disc 18 at the distal end; and plunger rod tip 20 (generally designated) extending from disc 18 designed to engage a plastic insert. Plunger rod tip 20 is integral with disc 18 and comprises: a neck portion 22 and a ball portion 24, the ball portion having slots 24a, 24b, 24c and 24d therein extending axially from the neck portion.

Figure 9:
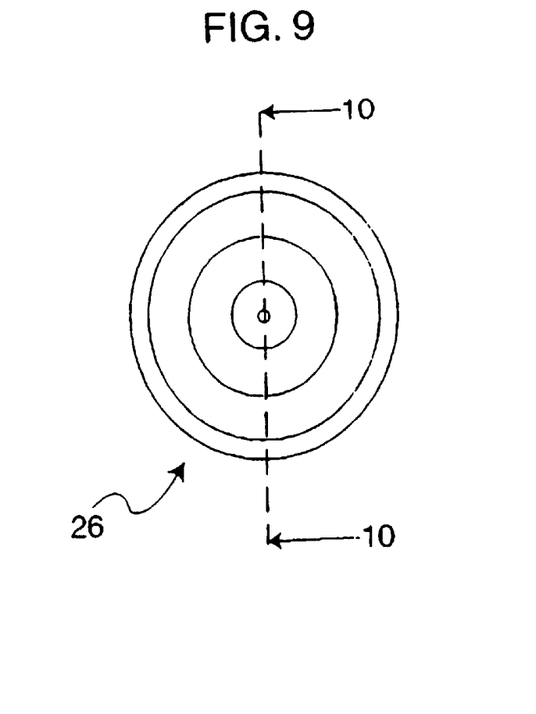
FIG. 9 is a top plan view of a plastic insert of the present invention which is to engage the plunger rod.
Figure 10:
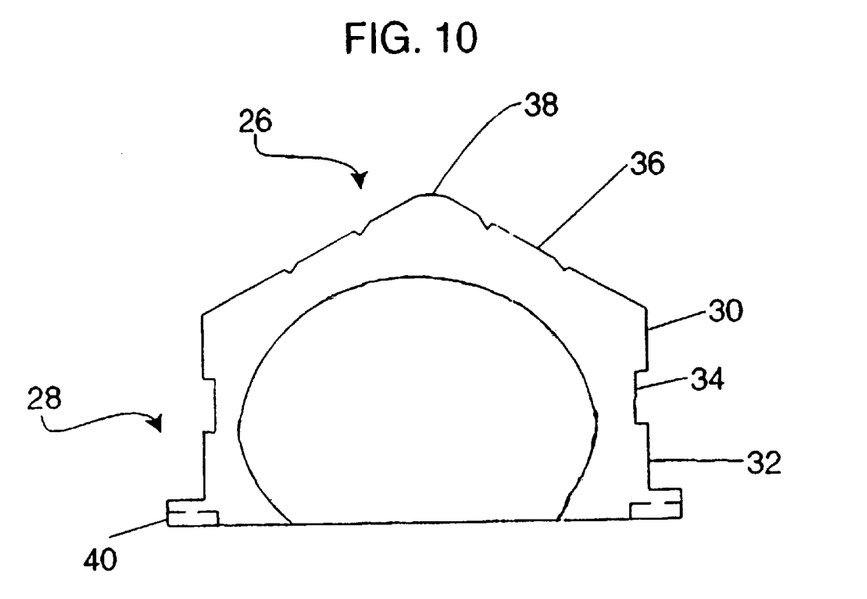
FIG. 10 is a cross-sectional view of the plastic insert taken along the line 10—10 of FIG. 9.

The self-aligning plunger rod 8 of the present invention is used in combination with a plastic insert, the top plan view of which is shown in FIG. 9. It is of a generally cone-shaped configuration best seen in FIG. 10 which is a cross-sectional view of the plastic insert, taken along the line 10—10 of FIG. 9. The plastic insert, generally designated by the numeral 26, comprises: a cylindrical shaft 28 having a distal end 30, and a proximal end 32; between the distal and proximal ends there is provided a cylindrical recess or groove 34; a cone-shaped head 36 extending from distal end 30 and terminating in zenith 38; and a cylindrical flange 40 extending from the proximal end 32.

Figure 11:
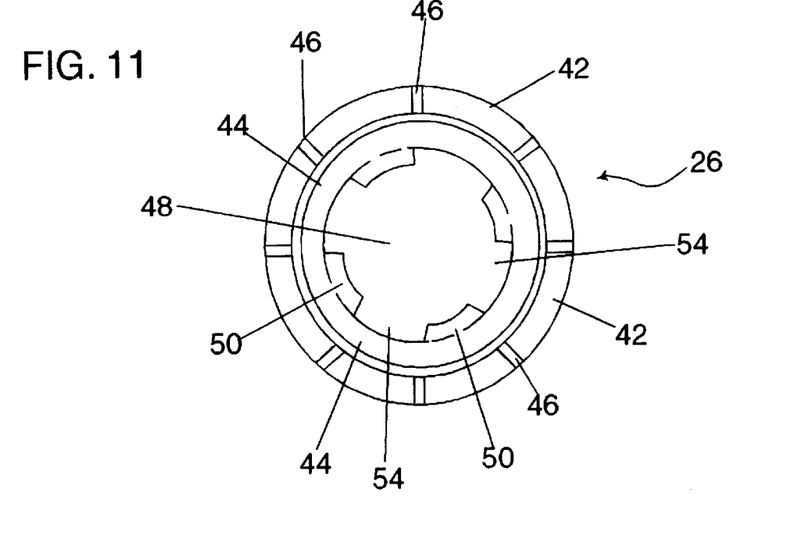
FIG. 11 is a bottom plan view of the plastic insert.

FIG. 11 shows a bottom plan view of the plastic insert 26 which comprises: a first cylindrical rim 42 constituting the underside of cylindrical flange 40; a second cylindrical rim 44 adjacent to said first cylindrical rim and projecting slightly above the horizontal surface of the first cylindrical rim; a plurality of reinforcing rods 46 connecting the first cylindrical rim 42 and the second cylindrical rim 44; a cavity 48 defined within said second cylindrical rim and the inside surface of the cone-shaped head 36; and a plurality of tabs 50 extending from the second cylindrical rim 44 into cavity 48. Between tabs 50 there are notches 52 to receive the slotted ball portion of the plunger rod tip.

Figure 1:
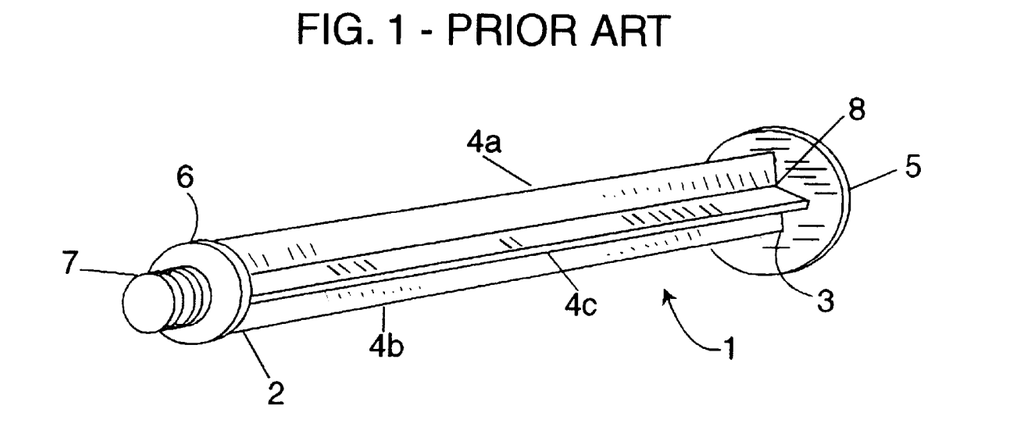
FIG. 1 is a prospective view of a prior art plunger rod.
Figure 2:
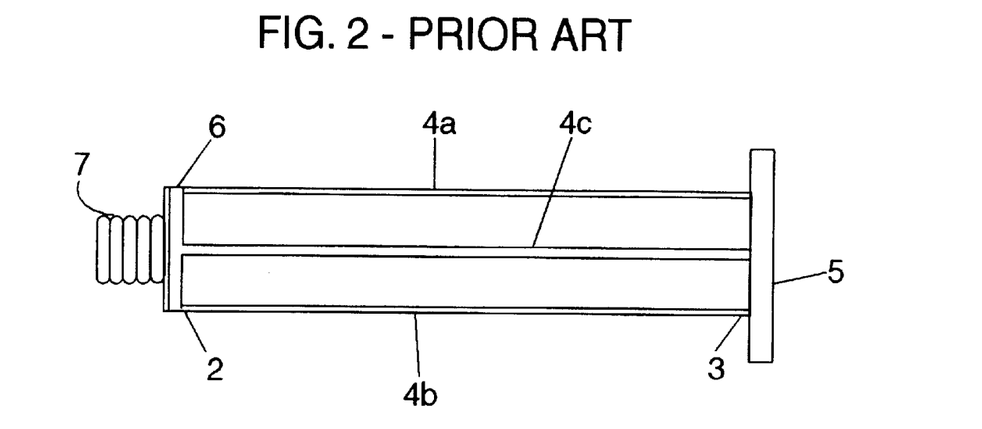
FIG. 2 is a side elevational view thereof.
Figure 3:
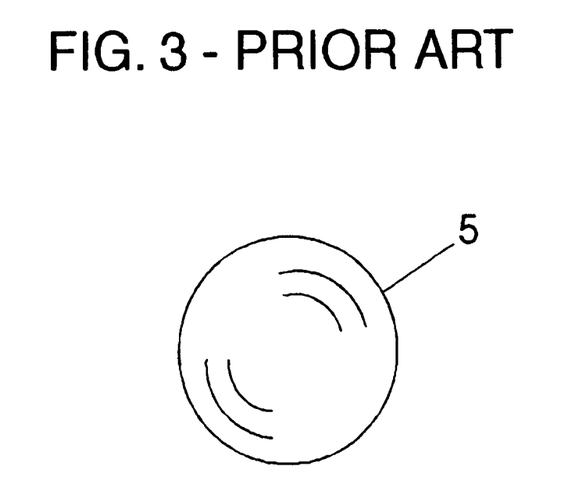
FIG. 3 is a bottom plan view thereof.
Figure 4:
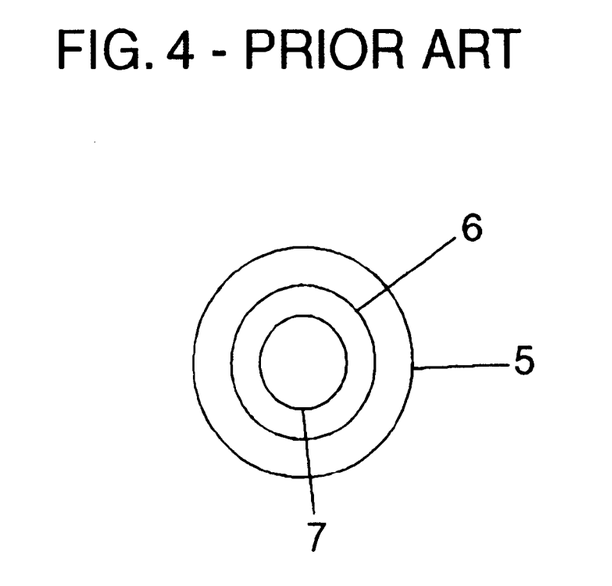
FIG. 4 is a top plan view thereof.
Figure 5:
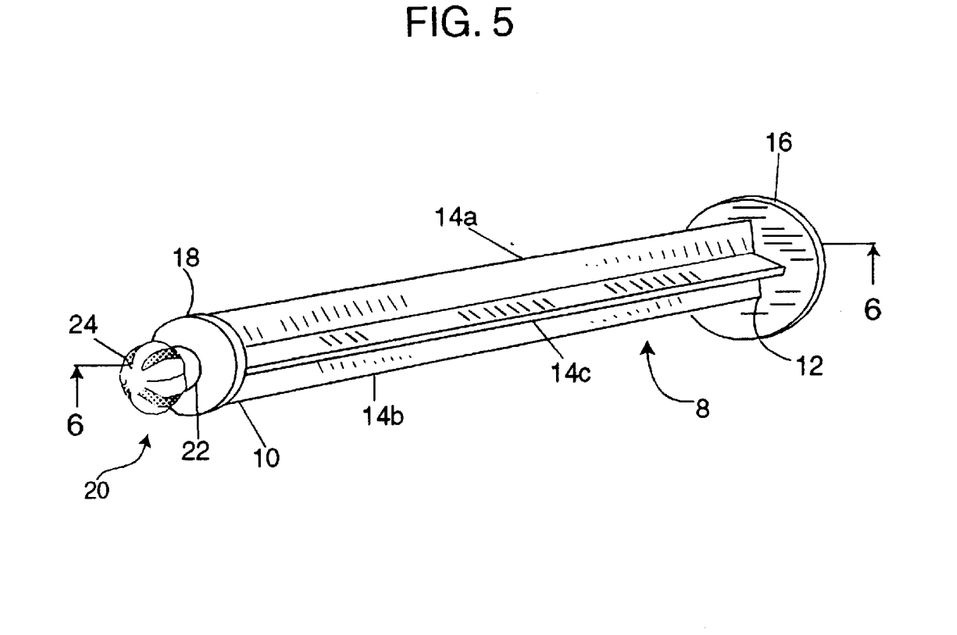
FIG. 5 is a perspective view of the plunger rod of the present invention.
Figure 6:
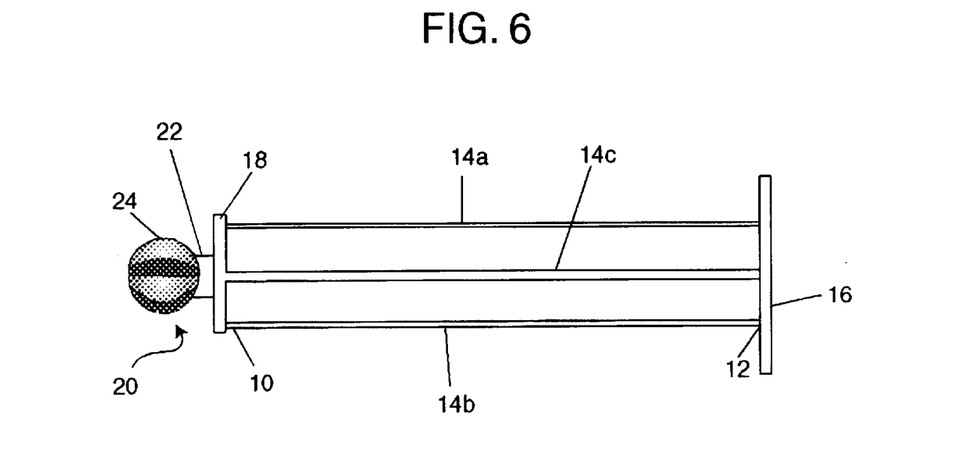
FIG. 6 is a cross-sectional view thereof taken along the line 6—6 of FIG. 5.
Figure 7:
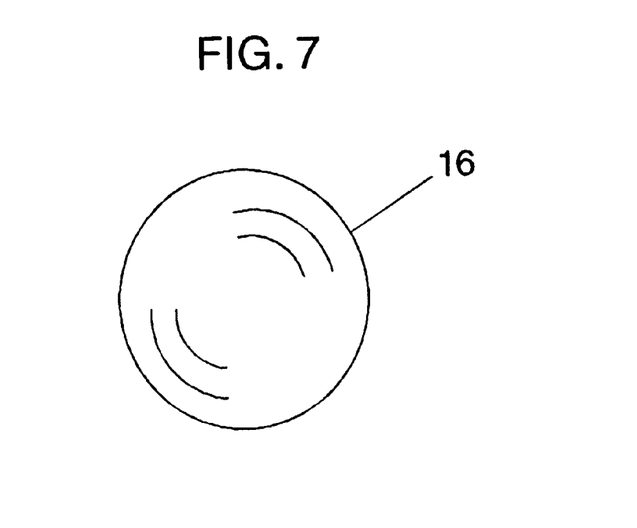
FIG. 7 is a bottom plan view thereof.
Figure 8:
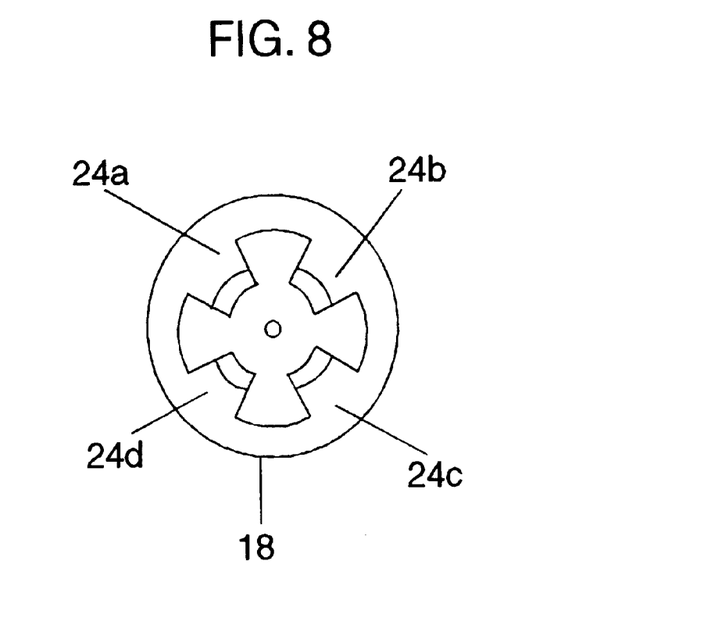
FIG. 8 is a top plan view thereof.

FIG. 11 shows: 8 reinforcing rods, however, less than 8 or more than 8 rods may be used; 4 tabs are shown, however, two or three tabs or more than four tabs may be used. Similarly, four slots are shown in FIG. 8 of the ball portion of the plunger rod tip. However, more or less slots may be used as long as the number of slots in the ball portion match the number of tabs in the plastic insert 26.

Figure 12:
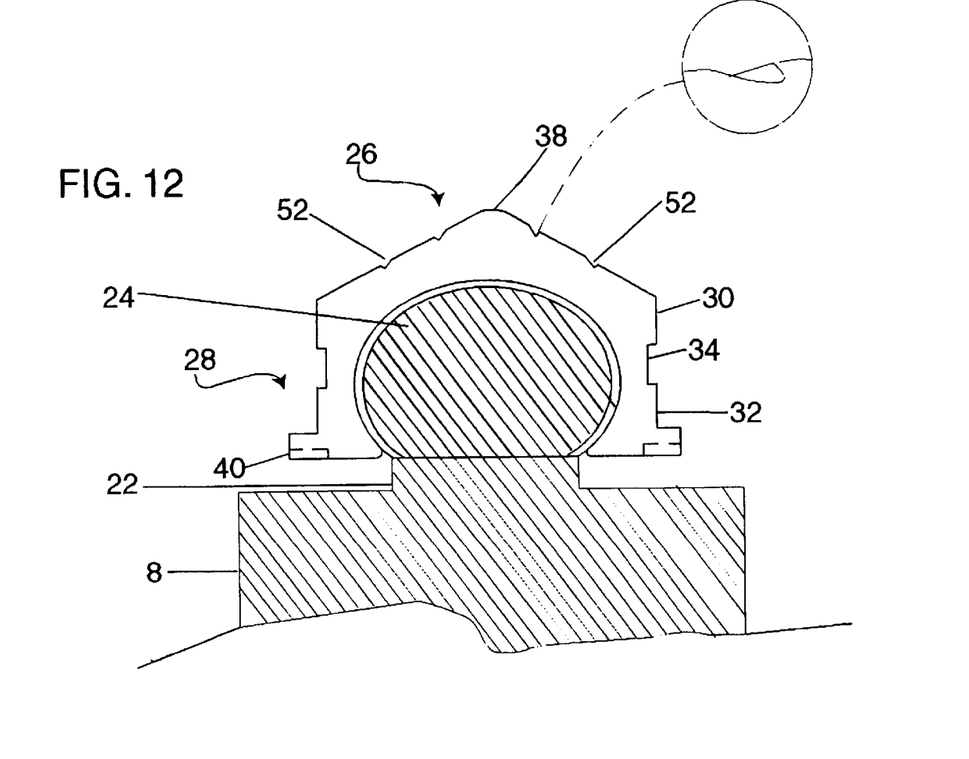
FIG. 12 shows in a partial cross-sectional view of the assembly of the plunger rod and the plastic insert.

FIG. 12 shows in a partial cross-sectional view the assembly of the self-aligning plunger rod 8 and the plastic insert combination 26. The ball portion 24 of the plunger rod tip 20 fits into the cavity or socket 48 of the cone-shaped head 36 and freely moves therein, essentially floating within the cavity or socket. Any external pressure on the plunger rod is directed in an axial direction and does not impact the integrity of the seal formed by an elastomeric plunger head cover (not shown) and the inside wall of a syringe or cartridge barrel (not shown).

As illustrated in FIG. 12, plastic insert 26 is adapted to receive various elastomeric plunger head covers (not shown) by virtue of the design of the plastic insert 26 having a cylindrical recess 34 to hold an oppositely configured elastomeric plunger head. In addition, cylindrical grooves 52 are designed to receive and hold different configurational elastomeric plunger head covers with slight protuberances therein to fit into the grooves 52 of the cone-shaped head 36 of the plastic insert 26.

In use, slots 24a, 24b, 24c and 24d of plunger rod tip 20 are aligned with cylindrical openings 54 in the plastic insert 26. The ball portion 24 of the plunger rod tip is inserted into the cavity 48 of the plastic insert. When inserted, the plunger rod is rotated ¼ turn and is held by tabs 50. To remove the plunger rod from the cavity of the plastic insert, the plunger rod is turned ¼ turn forward or backward.

Figure 13:
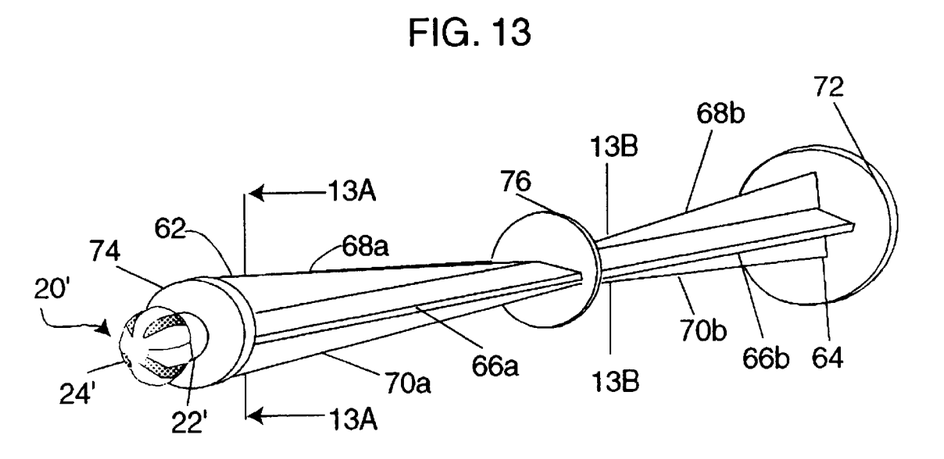
FIG. 13 is a perspective view of one embodiment of the present invention showing a reinforced plunger rod.
Figure 14:
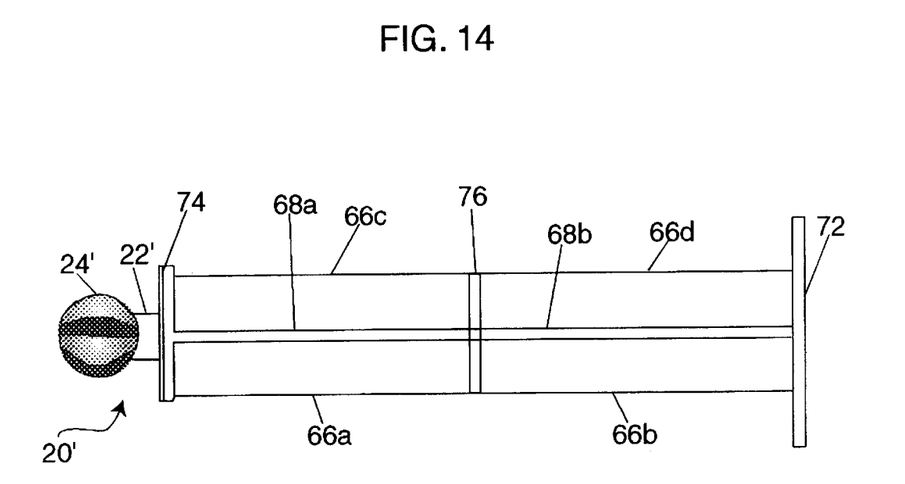
FIG. 14 is a side-elevational view of the reinforced plunger rod shown in FIG. 13.
Figure 15:
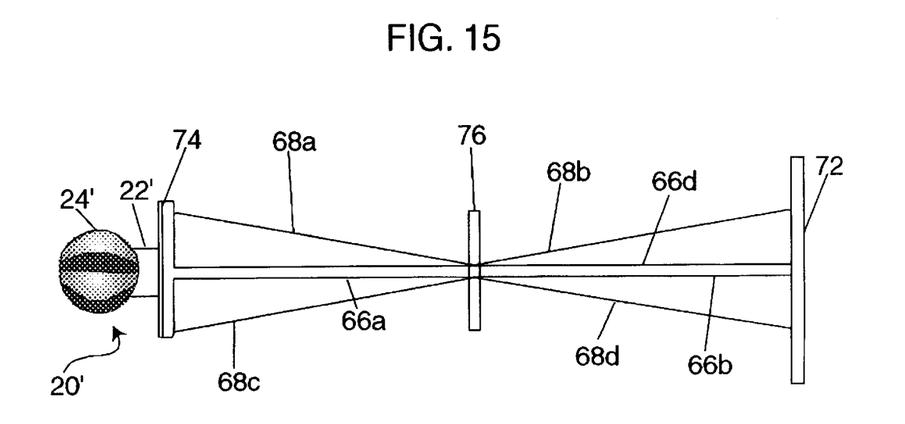
FIG. 15 is another side-elevational view of the reinforced plunger rod shown in FIG. 13 rotated 90° from that shown in FIG. 14.
Figure 16:
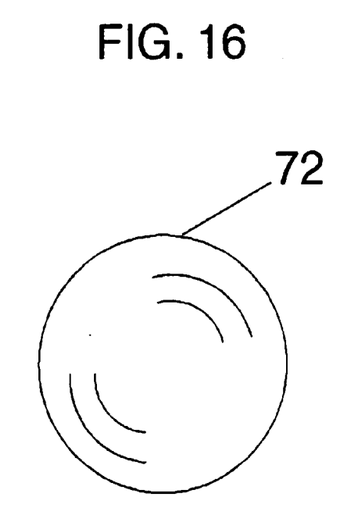
FIG. 16 is a bottom plan view of the reinforced plunger rod shown in FIG. 13.
Figure 17:
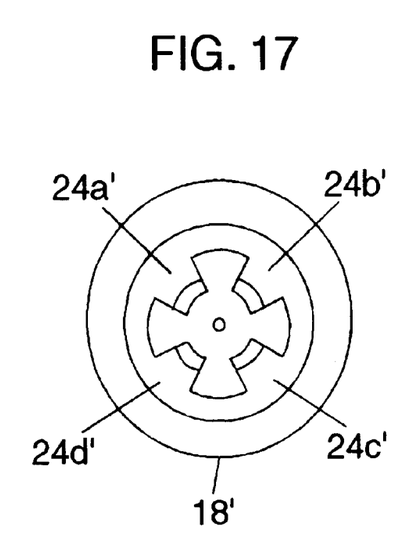
FIG. 17 is the top plan view of the reinforced plunger rod shown in FIG. 13.

FIGS. 13–17 show an embodiment of the present invention having a reinforced plunger rod used in combination with the plunger tip and plastic insert above-described, wherein:

FIG. 13 is a perspective view of the reinforced plunger rod;

FIG. 13A is a cross-sectional view of the reinforced plunger rod taken along the line 13A—13A of FIG. 13;

FIG. 13B is another cross-sectional view of the reinforced plunger rod taken along the line 13B—13B of FIG. 13;

FIG. 14 is a side-elevational view of the reinforced plunger rod shown in FIG. 13;

FIG. 15 is another side-elevational view of the reinforced plunger rod shown in FIG. 13 rotated 90° from that shown in FIG. 14;

FIG. 16 is a bottom plan view of the reinforced plunger rod shown in FIG. 13; and FIG. 17 is the top plan view of the reinforced plunger rod shown in FIG. 13.

Self-aligning reinforced plunger rod 60, having a distal end 62 and a proximal end 64 comprises:

longitudinally extending radial vanes 66a and 66b having a rectangular configuration;

longitudinally extending radial vanes 70a and 70b having a triangular configuration;

a thumb rest 72 at the proximal end;

a disc 74 at the distal end;

a central disc 76 located at about the mid point between thumb rest 72 and disc 74; and a plunger rod tip 20' (generally designated) extending form disc 74 designed to engage a plastic insert.

Plunger rod tip 20' is integral with disc 74 and comprises: a neck portion 22', and a ball portion 24', the ball portion having slots 24a', 24b', 24c' and 24d' therein extending axially from the neck portion.

The reinforced plunger rod 60 is used in combination with plastic insert 26 which is shown and described in FIGS. 9–12.

Figure 18:
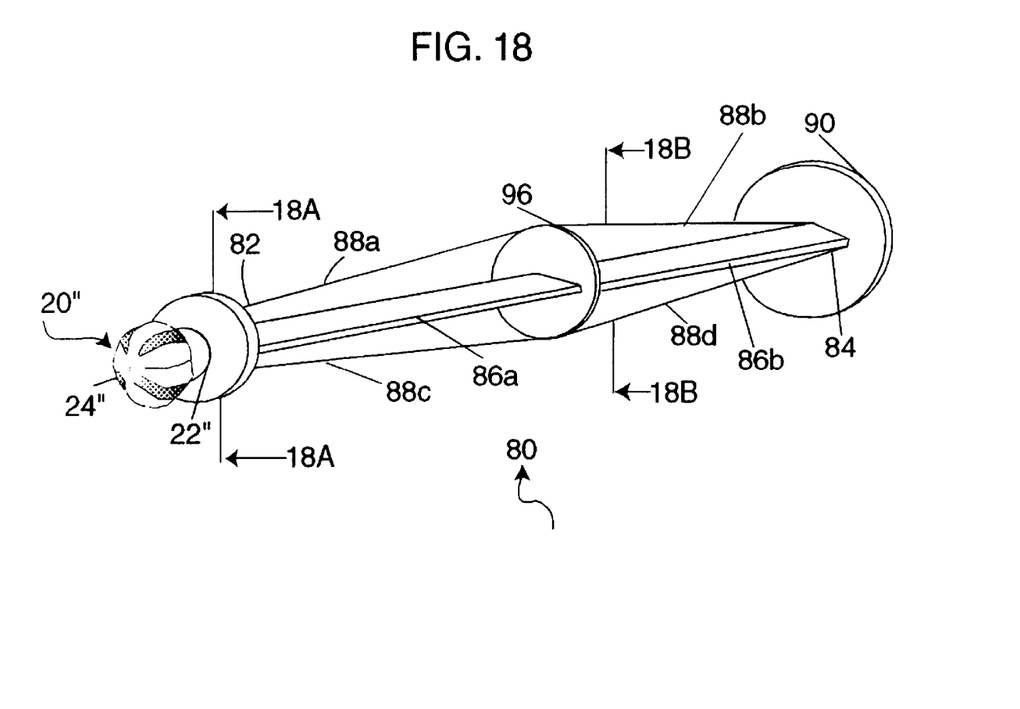
FIG. 18 is a perspective view of another embodiment of the present invention showing a reinforced plunger rod.
Figure 19:
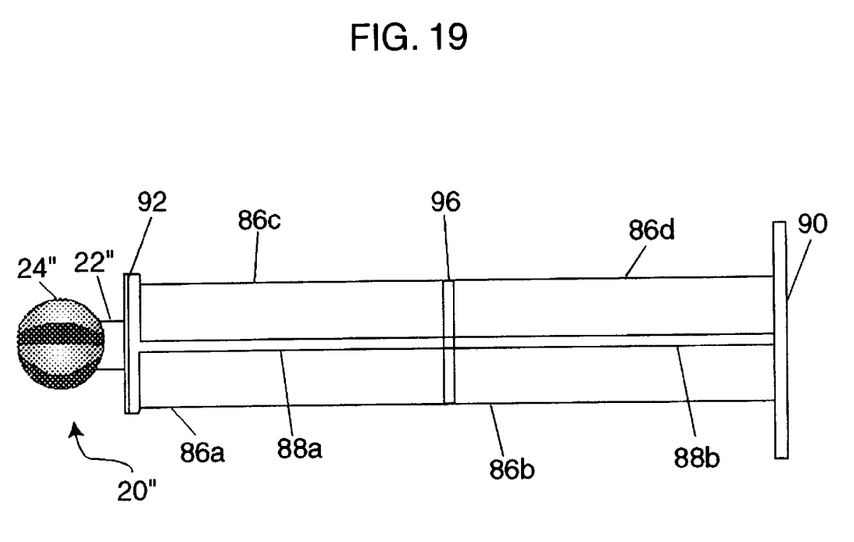
FIG. 19 is a side-elevational view of the reinforced plunger rod shown in FIG. 18.
Figure 20:
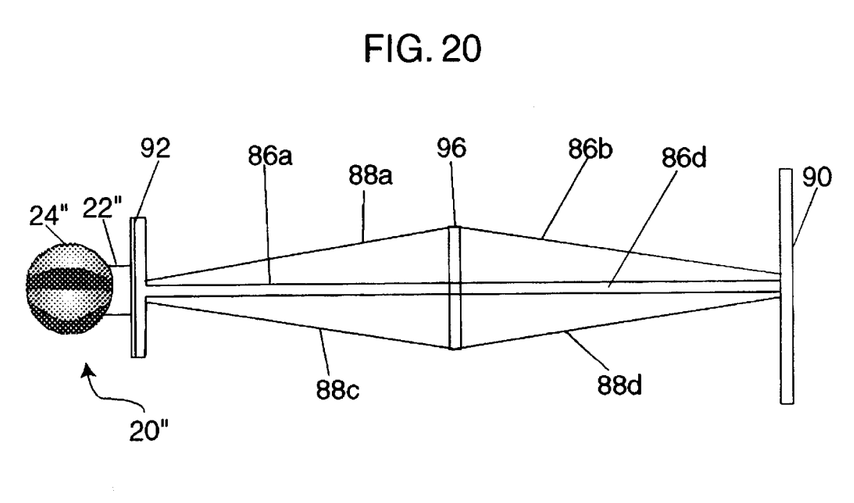
FIG. 20 is another side-elevational view of the reinforced plunger rod shown in FIG. 18 rotated 90° from that shown in FIG. 19.
Figure 21:
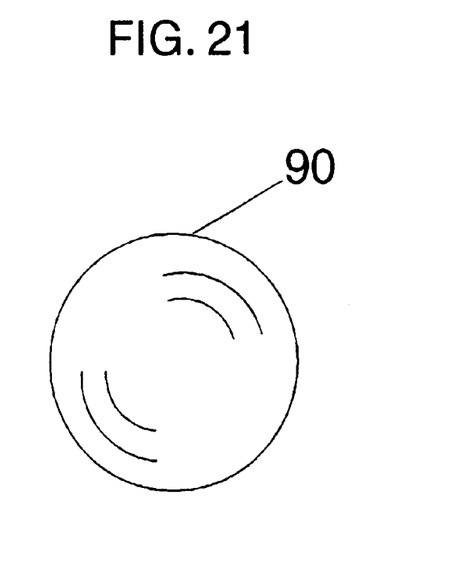
FIG. 21 is a bottom plan view of the reinforced plunger rod shown in FIG. 18.
Figure 22:
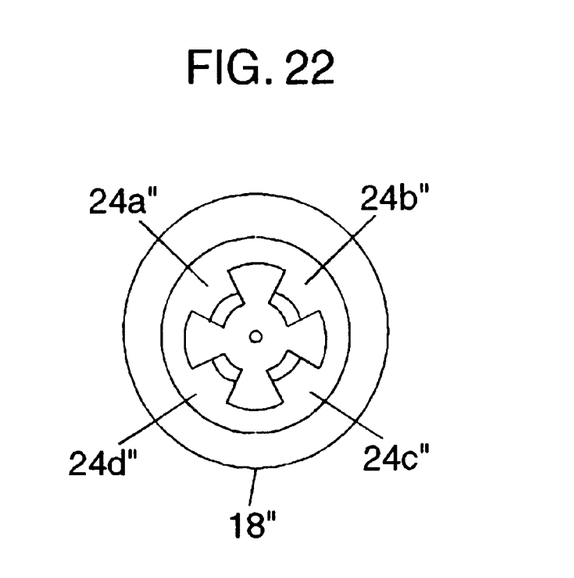
FIG. 22 is a top plan view of the reinforced plunger rod shown in FIG. 18.

FIGS. 18–22 show another embodiment of the present invention having a reinforced plunger rod used in combination with the plunger tip and plastic insert above-described, wherein:

FIG. 18 is a perspective view of the reinforced plunger rod;

FIG. 18A is a cross-sectional view of the reinforced plunger rod taken along the line 18A—18A of FIG. 18;

FIG. 18B is a cross-sectional view of the reinforced plunger rod taken along the line 18B—18B of FIG. 18;

FIG. 19 is a side-elevational view of the reinforced plunger rod shown in FIG. 18;

FIG. 20 is another side-elevational view of the reinforced plunger rod shown in FIG. 18 rotated 90° from that shown in FIG. 19;

FIG. 21 is a bottom plan view of the reinforced plunger rod shown in FIG. 18; and FIG. 22 is a top plan view of the reinforced plunger rod shown in FIG. 18.

Plunger rod 80 having a distal end 82 and a proximal end 84 comprises:

longitudinal radially extending vanes 86a, 86b, (86c and 86d are hidden in FIG. 18) having a rectangular configuration;

longitudinal radially extending vanes 88a, 88b, 88c and 88d having triangular configuration;

thumb rest 90 at the proximal end 84 of the plunger rod 80;

a disc 92 at the distal end 82 of the plunger rod;

plunger rod tip 94 extending from disc 92 designed to engage a plastic insert; and a central disc 96 located at about the mid point between thumb rest 90 and disc 92.

Central disc 96 supports the rectangular vanes and the triangular vanes and is integral therewith to provide dimensional stability to the plunger rod. Cross sectional view FIG. 18A taken along the line 18A—18A of FIG. 18 illustrates that at about the mid point of the plunger rod the rectangular and triangular vanes are about equal in size in the radial direction, however, while the rectangular vanes connecting to the central disc 96, disc 92 and thumb rest 90 maintain their rectangular configuration, the triangular vanes diminish in size in the radial direction as they approach disc 92 and thumb rest 90. As shown, the triangular vanes merge with the rectangular vanes at disc 92 and thumb rest 90. Cross-sectional view of the plunger rod in FIG. 18B, taken along the line 18B—18B of FIG. 18 shows that triangular vanes 88a, 88b, 88c and 88d diminish to a small size and merge with rectangular vanes 86a and 86b at disc 92 and thumb rest 90.

FIG. 19 shows the plunger rod of FIG. 18 in a side-elevational view where triangular vanes 88a and 88b are at the center of the Fig., and rectangular vanes 86a, 86b, 86c and 86d are at the sides of the Fig.

FIG. 20 is another side-elevational view of the plunger rod of FIG. 18 rotated 90° from that shown in FIG. 19. The triangular vanes 88a, 88b, 88c and 88d are at the sides of the Fig. and rectangular vanes 86a and 86d are at the center thereof.

FIGS. 21 and 22 show respectively the bottom and top plan views of the plunger rod.

Plunger rod tip 20" is integral with disc 92 and comprises:

a neck portion 22", and a ball portion 24", the ball portion having slots 24a", 24b", 24c" and 24d" therein extending axially from the neck portion.

The reinforced plunger rod 80 is used in combination with plastic insert 26 which is shown and described in FIGS. 9–12.

The plunger rods and the plastic insert assemblies of the present invention are made by injection molding, well-known in the art, using thermoplastic materials. Polypropylene, polyethylene and blends thereof are preferred for providing strength to the plunger rods. However, other polymers, such as polystyrenes, polyesters and polycarbonates may also be used.

| LIST OF REFERENCE NUMBERS USED | |
|---|---|
| PRIOR ART | |
| Plunger rod | 1 |
| Distal end of plunger rod | 2 |
| Proximal end of plunger rod | 3 |
| Vanes of plunger rod | 4a, 4b, 4c & 4d |
| Thimb rest | 5 |
| Disc | 6 |
| Screw threaded member | 7 |
| PRESENT INVENTION (FORST EMBODIMENT) | |
| Self-aligning plunger rod (generally designated) | 8 |
| Distal end of self-aligning pluger rod | 10 |
| Proximal end of self-aligning plunger rod | 12 |
| Longitudinal, radially extending vanes | 14a, 14b, 14c & 14d |
| Thumb rest at the proximal end | 16 |
| Disc at distal end | 18 |
| Plunger rod tip (generally designated) | 20 |
| Neck portion of plunger rod tip | 22 |
| Ball portion of plunger rod tip | 24 |
| Slots in ball portion | 24a, 24b, 24c & 24d |
| Plastic insert (generally designated) | 26 |
| Cylindrical shaft of plastic insert (generally designated) | 28 |
| Distal end of cylindrical shaft | 30 |
| Proximal end of cylindrical shaft | 32 |
| Cylindrical recess or groove in cylindrical shaft | 34 |
| Cone-shaped head | 36 |
| Zenith of cone-shaped head | 38 |
| Cylindrical flange of cylindrical shaft | 40 |
| First cylindrical rim on the underside of flange 40 | 42 |
| Second cylindrical rim | 44 |
| Plurality of reinforcing rods | 46 |
| Cavity inside of the cone-shaped head | 48 |
| Plurality of tabs extending into cavity 48 | 50 |
| Cylindrical notches in the outside surface of the ball portion of plastic insert | 52 |
| Cylindrical openings in the inside surface of plastic insert | 54 |
| PRESENT INVENTION (SECOND EMBODIMENT) | |
| Self-aligning plunger rod (generally designated) | 60 |
| Distal end of self-aligning plunger rod | 62 |
| Proximal end of self-aligning plunger rod | 64 |

-continued

LIST OF REFERENCE NUMBERS USED

| | |
|---|---|
| Longitudinal, radially extending vanes having a rectangular configuration | 66a, 66b, 66c & 66d |
| Longitudinal, radially extending vanes having a triangular configuration | 68a, 68b, 68c, 68d, 70a & 70b |
| Thumb rest | 72 |
| Disc at the distal end of plunger rod | 74 |
| Central disc | 76 |
| Plunger rod tip (generally designated) | 20' |
| Neck portion of plunger rod tip | 22' |
| Ball portion of plunger rod tip | 24' |
| Slots in ball portion | 24a', 24b', 24c' & 24d' |

PRESENT INVENTION (THIRD EMBODIMENT)

| | |
|---|---|
| Plunger rod | 80 |
| Distal end of plunger rod | 82 |
| Proximal end of plunger rod | 84 |
| Longitudinal radially extending vanes having a rectangular configuration | 86a, 86b, 86c & 86d |
| Longitudinal radially extending vanes having a triangular configuration | 88a, 88b, 88c & 88d |
| Thumb rest | 90 |
| Disc at distal end | 92 |
| Central disc | 96 |
| Plunger rod tip (generally designated) | 20" |
| Neck portion of plunger rod tip | 22" |
| Ball portion of plunger rod tip | 24" |
| Slots in ball portion | 24a", 24b", 24c" & 24d" |

Various modifications of the present invention will become apparent to those skilled in the art. This invention is intended to include such modifications to be limited only by the scope of the claims.

What is claimed is:

1. A self-aligning plunger rod and non-elastomeric plastic plunger insert assembly for use with an elastomeric plunger in a cartridge or syringe barrel for manual or power-assisted withdrawing of fluid from a site or expelling fluid from the cartridge or syringe barrel comprising:
   a) a plunger rod having a distal end and a proximal end comprising:
      longitudinal radially extending vanes;
      a thumb rest at the proximal end;
      a disc at the distal end; and
      a plunger rod tip extending from said disc adapted to engage a plastic plunger insert, said plunger rod tip comprising a neck portion and a ball portion, said ball portion having slots therein extending axially from said neck portion;
   b) a non-elastomeric plastic plunger insert comprising:
      a cylindrical shaft having a distal end and a proximal end;
      at least one cylindrical recess between the distal end and the proximal end of said cylindrical shaft adapted to hold an elastomeric plunger having a cylindrical protuberance to engage said cylindrical recess;
      a cone-shaped head having an inside surface and an outside surface, extending from the distal end of said cylindrical shaft;
      a cylindrical flange extending from the proximal end of said cylindrical shaft;
      a first cylindrical rim constituting an underside of said cylindrical flange;
      a second cylindrical rim adjacent to said first cylindrical rim and projecting slightly above a horizontal surface of said first cylindrical rim;
      a cavity defined within said second cylindrical rim and the inside surface of said cone-shaped head;
      a plurality of tabs extending from the second cylindrical rim into said cavity; and
      notches between said tabs to receive said slotted ball portion of said plunger rod tip.

2. The self-aligning plunger rod and non-elastomeric plastic plunger insert assembly of claim 1 wherein said cone-shaped head terminates in a zenith.

3. The self-aligning plunger rod and non-elastomeric plastic plunger insert assembly of claim 1 further comprising a plurality of reinforcing rods connecting said first cylindrical rim and said second cylindrical rim.

4. The self-aligning plunger rod and non-elastomeric plastic plunger insert assembly of claim 1 wherein the number of tabs in said non-elastomeric plastic insert matches the number of slots in said ball portion of said plunger rod tip.

5. The self-aligning plunger rod and non-elastomeric plastic plunger insert assembly of claim 4 wherein the number of tabs in the non-elastomeric plastic insert is 2–10 and the number of slots in the ball portion of said plunger rod is 2–10.

6. The self-aligning plunger rod and non-elastomeric plastic plunger insert assembly of claim 1 wherein said outside surface of said cone-shaped head is provided with at least one cylindrical groove for engagement with a protuberance in an elastomeric plunger.

7. A self-aligning reinforced plunger rod and non-elastomeric plastic plunger insert assembly for use with an elastomeric plunger in a cartridge or syringe barrel for manual or power-assisted withdrawing of fluid from a site or expelling fluid from the cartridge or syringe barrel comprising:
   a) a plunger rod body having a distal end and a proximal;
      an end disc at said distal end;
      a plunger rod tip extending from said end disc adapted to engage a non-elastomeric plastic plunger insert, said plunger rod tip comprising: a neck portion; and a ball portion having slots therein extending axially from said neck portion;
      a thumb rest at said proximal end for facilitating exertion of an external pressure on said plunger rod body;
      a reinforcing disc at about the longitudinal mid-point of said plunger rod body;
      a first pair of rectangular radially extending vanes connecting said end disc and said reinforcing disc;
      a second pair of rectangular radially extending vanes connecting said reinforcing disc and said thumb rest;
      a first pair of isosceles triangular radially extending vanes connecting said end disc and said reinforcing disc, wherein the smallest angle of said isosceles triangular vanes point toward said reinforcing disc; and
      a second pair of isosceles triangular radially extending vanes connecting said reinforcing disc and said thumb rest, wherein the smallest angle of said isosceles triangular vanes point toward said reinforcing disc, wherein:
         said first pair of rectangular radially extending vanes and said first pair of isosceles triangular radially extending vanes are integral with each other and with said end disc and said reinforcing disc; and
         said second pair of said rectangular radially extending vanes and said second pair of isosceles triangular radially extending vanes are integral with each other and with said reinforcing disc and said thumb rest;

b) a non-elastomeric plastic plunger insert comprising:
  a cylindrical shaft having a distal end and a proximal end;
  at least one cylindrical recess between the distal end and the proximal end of said cylindrical shaft adapted to hold an elastomeric plunger having a cylindrical protuberance to engage said cylindrical recess;
  a cone-shaped head having an inside surface and an outside surface, extending from the distal end of said cylindrical shaft;
  a cylindrical flange extending from the proximal end of said cylindrical shaft;
  a first cylindrical rim constituting an underside of said cylindrical flange;
  a second cylindrical rim adjacent to said first cylindrical rim and projecting slightly above a horizontal surface of said first cylindrical rim;
  a cavity defined within said second cylindrical rim and the inside surface of said cone-shaped head;
  a plurality of tabs extending from the second cylindrical rim into said cavity; and
  notches between said tabs to receive said slotted ball portion of said plunger rod tip.

8. The self-aligning reinforced plunger rod and non-elastomeric plastic plunger insert assembly of claim 7 further comprising a plurality of reinforcing rods connecting said first cylindrical rim and said second cylindrical rim.

9. The self-aligning reinforced plunger rod and non-elastomeric plastic plunger insert assembly of claim 7 wherein the number of tabs in said non-elastomeric plastic insert matches the number of slots in said ball portion of said plunger rod tip.

10. The self-aligning reinforced plunger rod and non-elastomeric plastic plunger insert assembly of claim 9 wherein the number of tabs in the non-elastomeric plastic insert is 2–10 and the number of slots in the ball portion of said plunger rod is 2–10.

11. The self-aligning reinforced plunger rod and non-elastomeric plastic plunger insert assembly of claim 7 wherein said outside surface of said cone-shaped head is provided with at least one cylindrical groove for engagement with a protuberance in an elastomeric plunger.

12. The self-aligning reinforced plunger rod and non-elastomeric plastic plunger insert assembly of claim 7 made of a thermoplastic material.

13. The self-aligning reinforced plunger rod and non-elastomeric plastic plunger insert assembly of claim 7 made of a polymeric material selected from the group consisting of polystyrenes, polyesters and polycarbonates.

14. A self-aligning reinforced plunger rod and non-elastomeric plastic plunger insert assembly for use with an elastomeric plunger in a cartridge or syringe barrel for manual or power-assisted withdrawing of fluid from a site or expelling fluid from the cartridge or syringe barrel comprising:
  a) a plunger rod body having a distal end and a proximal; an end disc at said distal end;
    a plunger rod tip extending from said end disc adapted to engage a non-elastomeric plastic plunger insert, said plunger rod tip comprising: a neck portion; and a ball portion having slots therein extending axially from said neck portion;
    a thumb rest at said proximal end for facilitating exertion of an external pressure on said plunger rod body;
    a reinforcing disc at about the longitudinal mid-point of said plunger rod body;
    a first pair of rectangular radially extending vanes connecting said end disc and said reinforcing disc;
    a second pair of rectangular radially extending vanes connecting said reinforcing disc and said thumb rest;
    a first pair of isosceles triangular radially extending vanes connecting said end disc and said reinforcing disc, wherein the smallest angle of said isosceles triangular vanes point toward said reinforcing disc; and
    a second pair of isosceles triangular radially extending vanes connecting said reinforcing disc and said thumb rest, wherein the smallest angle of said isosceles triangular vanes point toward said thumb rest, wherein:
      said first pair of rectangular radially extending vanes and said first pair of isosceles triangular radially extending vanes are integral with each other and with said end disc and said reinforcing disc; and
      said second pair of rectangular radially extending vanes and said second pair of isosceles triangular radially extending vanes are integral with each other and with said reinforcing disc and said thumb rest;
  b) a non-elastomeric plastic plunger insert comprising:
    a cylindrical shaft having a distal end and a proximal end comprising;
    at least one cylindrical recess between the distal end and the proximal end of said cylindrical shaft adapted to hold an elastomeric plunger having a cylindrical protuberance to engage said cylindrical recess;
    a cone-shaped head having an inside surface and an outside surface, extending from the distal end of said cylindrical shaft;
    a cylindrical flange extending from the proximal end of said cylindrical shaft;
    a first cylindrical rim constituting an underside of said cylindrical flange;
    a second cylindrical rim adjacent to said first cylindrical rim and projecting slightly above a horizontal surface of said first cylindrical rim;
    a cavity defined within said second cylindrical rim and the inside surface of said cone-shaped head;
    a plurality of tabs extending from the second cylindrical rim into said cavity; and
    notches between said tabs to receive said slotted ball portion of said plunger rod tip.

15. The self-aligning reinforced plunger rod and non-elastomeric plastic plunger insert assembly of claim 14 further comprising a plurality of reinforcing rods connecting said first cylindrical rim and said second cylindrical rim.

16. The self-aligning reinforced plunger rod and non-elastomeric plastic plunger insert assembly of claim 14 wherein the number of tabs in said non-elastomeric plastic insert matches the number of slots in said ball portion of said plunger rod tip.

17. The self-aligning reinforced plunger rod and non-elastomeric plastic plunger insert assembly of claim 16 wherein the number of tabs in the non-elastomeric plastic insert is 2–10 and the number of slots in the ball portion of said plunger rod is 2–10.

18. The self-aligning reinforced plunger rod and non-elastomeric plastic plunger insert assembly of claim 14 wherein said outside surface of said cone-shaped head is provided with at least one cylindrical groove for engagement with a protuberance in an elastomeric plunger.

19. The self-aligning reinforced plunger rod and non-elastomeric plastic plunger insert assembly of claim 14 made of a thermoplastic material.

20. The self-aligning reinforced plunger rod and non-elastomeric plastic plunger insert assembly of claim 14 made of a polymeric material selected from the group consisting of polystyrenes, polyesters and polycarbonates.

* * * * *